United States Patent [19]

Ghebre-Sellassie et al.

[11] Patent Number: 4,912,146
[45] Date of Patent: Mar. 27, 1990

[54] COATED DOSAGE FORMS

[75] Inventors: Isaac Ghebre-Sellassie, Stanhope; Russell U. Nesbitt, Somerville, both of N.J.

[73] Assignee: Warner-Lambert Company, Morris Plains, N.J.

[21] Appl. No.: 64,916

[22] Filed: Oct. 30, 1987

Related U.S. Application Data

[63] Continuation-in-part of Ser. No. 696,945, Jan. 30, 1985, abandoned, and a continuation of Ser. No. 869,503, May 30, 1986, abandoned.

[51] Int. Cl.$^4$ ............................................... C08K 3/34
[52] U.S. Cl. .................................... 524/447; 523/105; 524/451; 524/560
[58] Field of Search ................ 523/105; 524/447, 451, 524/560

[56] References Cited

U.S. PATENT DOCUMENTS

| | | | |
|---|---|---|---|
| 2,897,121 | 7/1959 | Wagner | 424/497 |
| 3,909,444 | 9/1976 | Anderson et al. | 252/316 |
| 3,935,326 | 1/1976 | Groppenbacher et al. | 427/3 |
| 4,017,647 | 4/1977 | Ohno et al. | 427/3 |
| 4,321,117 | 3/1982 | Kaetsu et al. | 521/28 |
| 4,497,847 | 2/1985 | Kurlhara et al. | 427/3 |
| 4,749,731 | 6/1988 | Kyminas et al. | 524/447 X |

FOREIGN PATENT DOCUMENTS

| | | | |
|---|---|---|---|
| 0060023 | 9/1982 | European Pat. Off. | 427/3 |
| 0080341 | 1/1983 | European Pat. Off. | |
| 2476485 | 8/1981 | France | 427/3 |
| 8000659 | 4/1980 | Int'l Pat. Institute | 427/3 |
| 0109413 | 6/1983 | Japan | 427/3 |

*Primary Examiner*—Joseph L. Schofer
*Assistant Examiner*—J. M. Reddick
*Attorney, Agent, or Firm*—Ronald A. Daignault

[57] ABSTRACT

A coating composition and dosage form containing said coated composition and method for increasing the water permeability of a coated dosage form is described where the coating composition contains a water-dispersible polymer such as a copolymer of poly(meth)acrylic esters and water-insoluble inorganic substances such as kaolin wherein such coated particles are then overcoated with water-soluble hydrophilic polymers.

1 Claim, 6 Drawing Sheets

○ SIMULATED GASTRIC FLUID
□ SIMULATED INTESTINAL FLUID
♦ WATER

Figure 1:
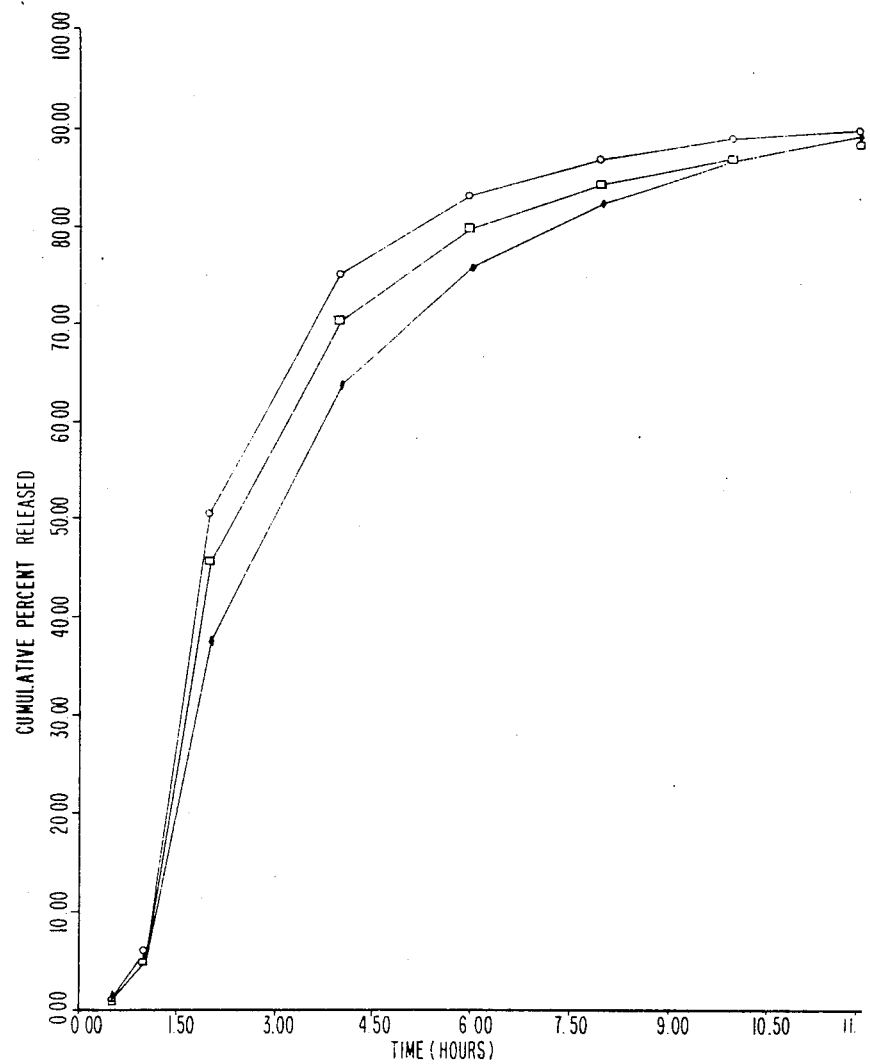
Figure 2:
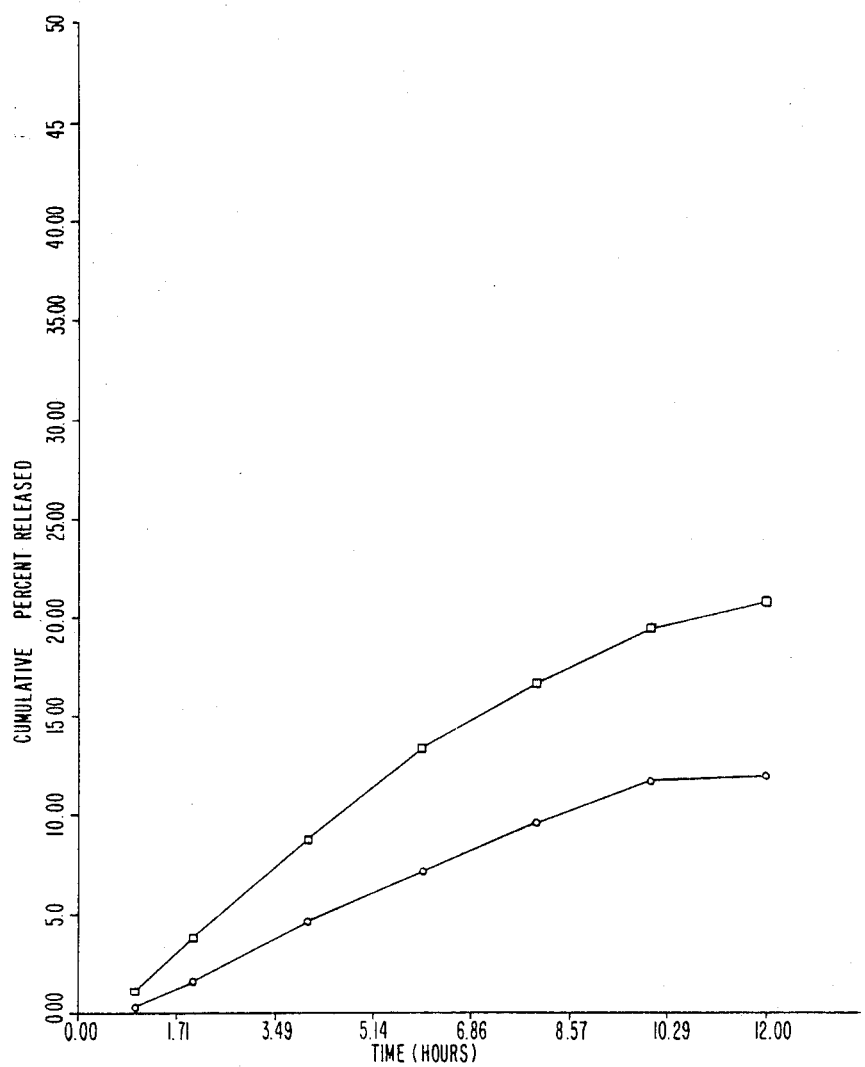
Figure 3:
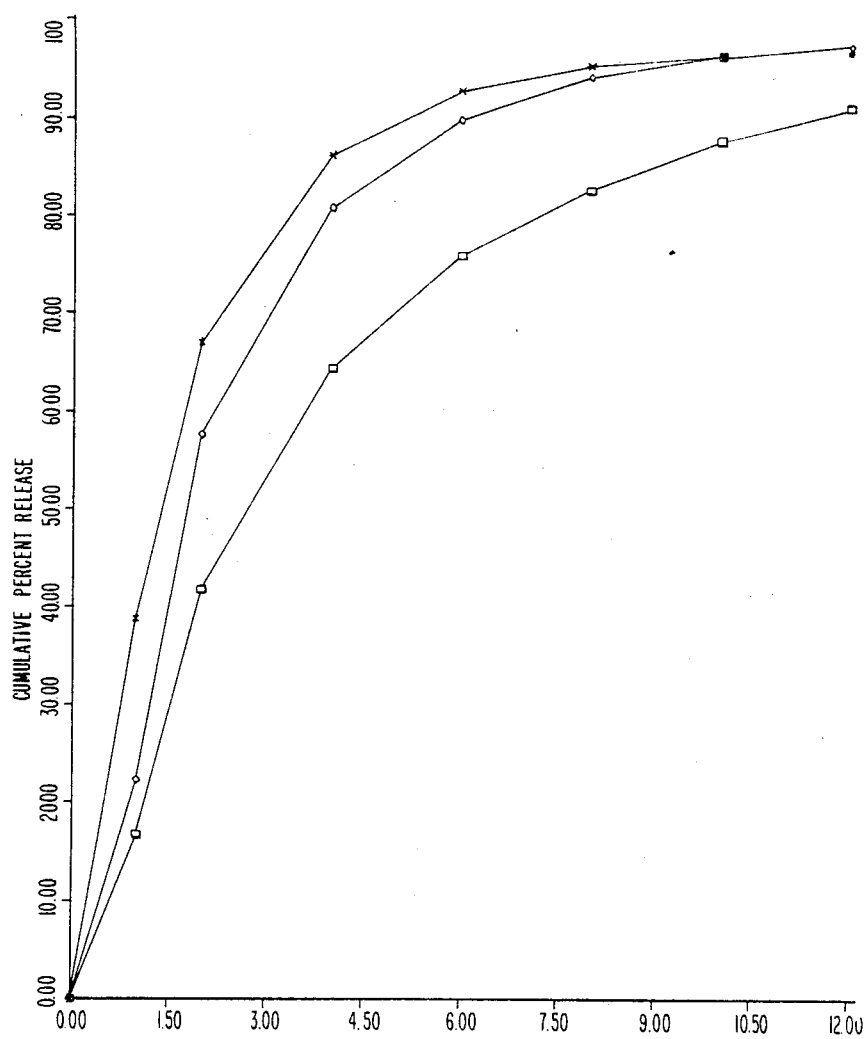
Figure 4:
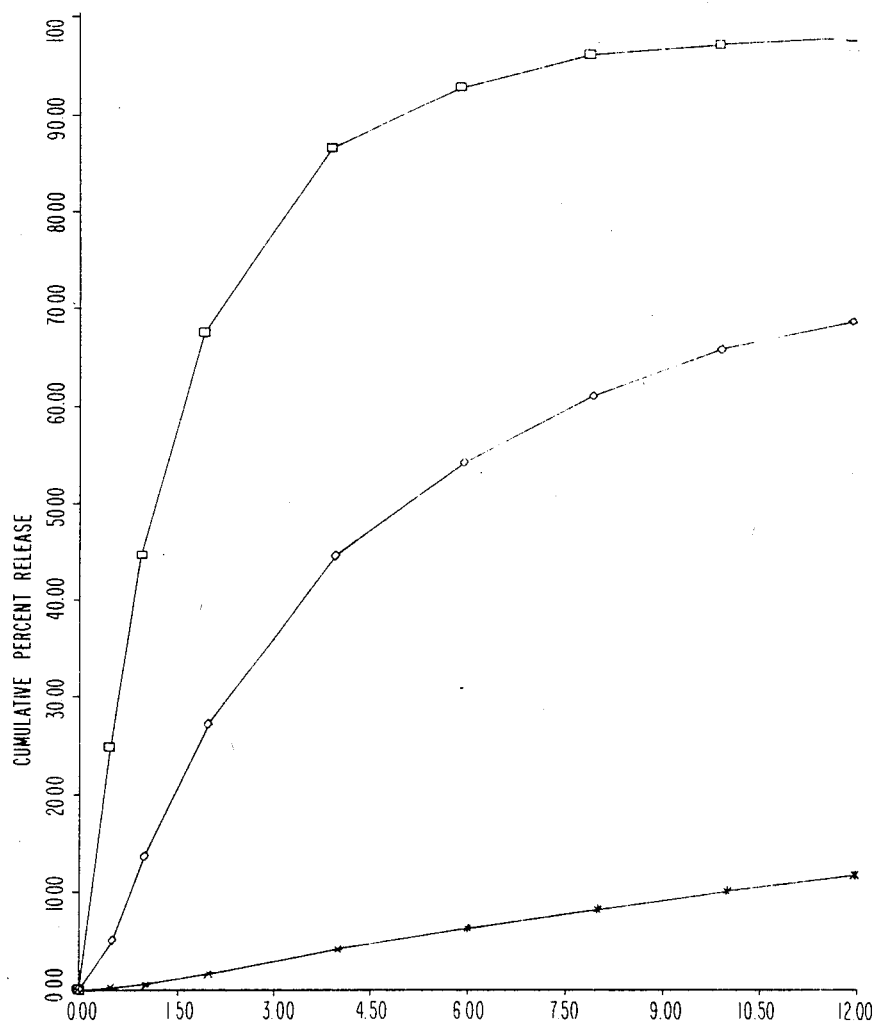

Fig. 2  □ 18% AND ○ 22% COATING LEVELS

□ 3.1, ◇ 3.2, ✱ 1:1 (DISSOLUTION MEDIUM: WATER)

□ 4%, ◇ 9%, ✷ 20% (DISSOLUTION MEDIUM WATER)

Figure 5:
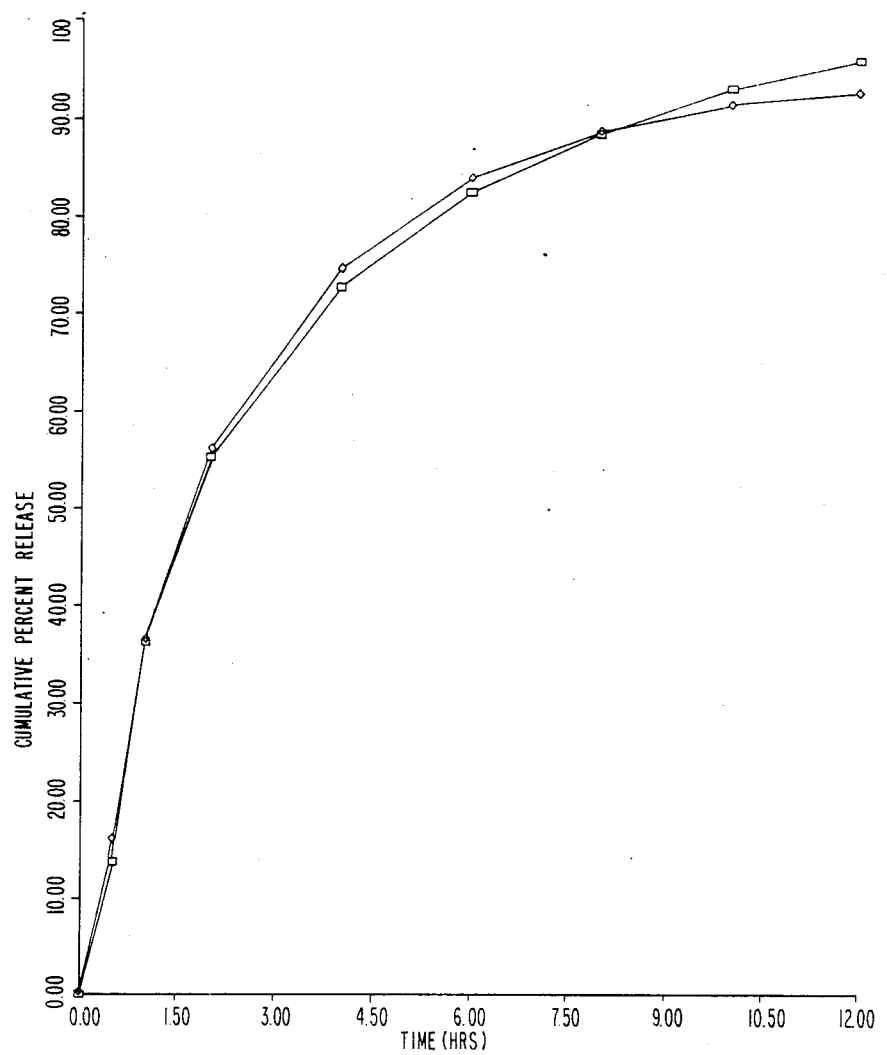
Figure 6:
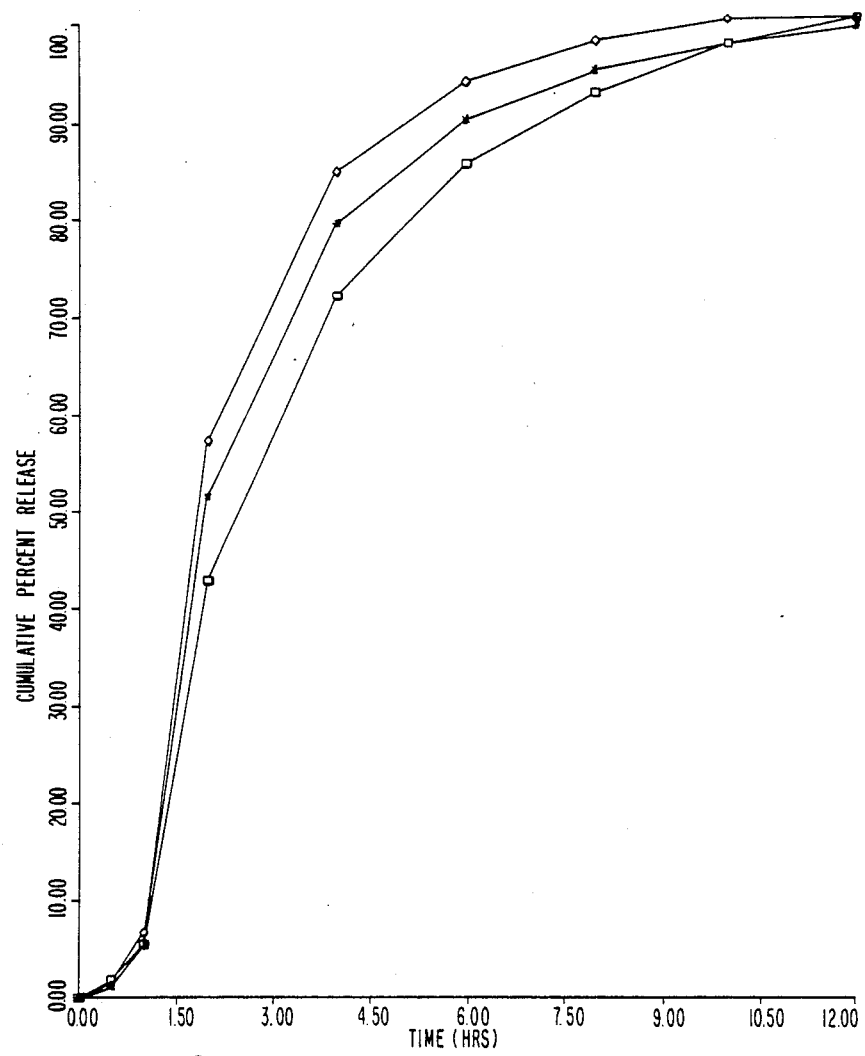

Fig. 5   □ RELEASE PROFILE OF DIPHENHYDRAMINE

4,912,146

COATED DOSAGE FORMS

CROSS-REFERENCE TO RELATED APPLICATION

This is a continuation-in-part of U.S. application Ser. No. 696,945 filed Jan. 30, 1985 now abandoned "which is a continuation of U.S. application Ser. No. 869,503, filed May 30, 1986, now abandoned."

BACKGROUND

The coating of physiologically-active substances with polymeric materials is well-known. The formulation of suitable coating materials has centered on obtaining suitable release properties for the final dosage form while minimizing the handling problems generally associated with coated products.

THE INVENTION

It has been discovered that unique combinations containing a water-dispersible polymer and water-insoluble inorganic substances (release modifiers) can be employed in coating formulations for physiologically-active substances, e.g., drugs.

In a preferred embodiment, a suspension of kaolin in water combined with an aqueous dispersion of a copolymer of poly(meth)acrylic esters, e.g., "Eudragit E 30 D", yields a coated dosage form having desirable sustained release properties. The coated particles are then overcoated with water-soluble hydrophilic polymers to improve product handling. The overcoat does not affect the release profiles of the coated products.

ADVANTAGES

The invention has several advantages over prior art dosage forms and methods of making them.

First, the inorganic release modifiers present in the formulations of the invention increase the water permeability of the coated dosage forms in direct proportion to their presence in the coating formulations. That is, the greater the concentration of kaolin or other suitable inorganic additive, the greater is the permeability of the coating after the dosage form has been ingested. This proportionality makes it possible to tailor the release properties of the dosage form to some extent.

Secondly, the need for one or more hydrophilic film-formers, e.g., hydropropylmethylcellulose, as release modifiers is obviated as taught in U.S. Pat. No. 3,935,326. Replacement of these expensive soluble additives by the insoluble release modifiers reduces overall cost.

Third, the need for a fourth compound in the formulation for reducing tackiness during processing as stated in U.S. Pat. No. 3,935,326 is obviated since the inorganic release modifiers employed in this invention act as antiadherents.

Since the inorganic modifiers used herein need not be treated, e.g., by milling or contacting with processing aids, prior to their inclusion in the coatings, substantial energy and time savings are achieved. Untreated kaolin is highly preferred as a filler since it can generally be used as received, needing milling only if the particles cannot be substantially uniformly dispersed.

Other aspects and advantages of the invention will become apparent from a consideration of the following drawings and description of the invention.

DESCRIPTION OF THE INVENTION

The Dosage Form

The invention centers on a unique combination of water dispersible polymers and water insoluble inorganic substances which, when brought together in proper amounts, produce the advantages set out herein.

Polymers

The polymeric matrices on which the polymer/inorganic release modifier combinations of the invention are based are water dispersible polymers containing functional groups in their backbones. In other words, the polymers useful herein may be any polymer having a high adsorption capacity; more preferably, they are neutral so that they are not affected by the pH gradient which prevails in the gastrointestinal tract. That is, a pH of about 1 to about 8 will not affect the subject polymers.

Useful polymers include those sold as aqueous dispersions having low viscosity and the requisite solubility when applied in pharmaceutical coatings. Generally, they are emulsion polymerized acrylic resins produced using one or more monomeric alkyl esters of acrylic or methacrylic acids. Preferably, they are emulsion polymerization products, poly (meth)acrylates, the resultant polymers containing no undesirable ionizable groups.

One preferred polymer is commercially available as "Eudragit E 30 D." This product is available from Rohn Pharma GmbH of Darmstadt, Federal Republic of Germany. "Eudragit E 30 D" is an aqueous dispersion of an acrylic resin which is neutral in character. Its polymeric structure contains units of structure $-CH_2-CRR^1-$, wherein R is $-H$ or $-CH_3$ and $R^1$ is $-C(O)OCH_3$ or $-C(O)OC_2H_5$. It has an average molecular weight of about 800,000 and a viscosity of $<50$ cp at 20° C., as measured with a Brookfield viscometer with adapter 6 r.p.m., according to DAB VII, page 20, subsection 31.

Another preferred polymer is commercially available as "Eudragit RL/RS." These are copolymers synthesized from acrylic and methacrylic acid esters with a low content of quarternary ammonium groups.

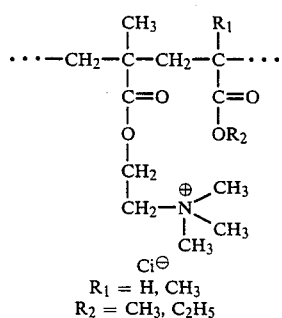

$R_1 = H, CH_3$
$R_2 = CH_3, C_2H_5$

The molar ratio of these ammonium groups to the remaining neutral (meth)acrylic acid esters is 1:20 with Eudragit RL and 1:40 with Eudragit RS. The mean molecular weight is approximately 150,000. It is recommended that plasticisers be added to enhance the characteristics of the film.

Since the polymers are to be admixed with the inorganic modifiers of the invention in an aqueous environment, it is generally preferred that the polymer particles have diameters on the order of 0.01 to 1 mm. Sizes corresponding to a coagulum content of 500 mg =0.5% maximum are preferred.

In optional embodiments, one or more overcoats are applied to the dosage forms which have been coated with a polymer inorganic additive coating composition. These overcoats contain a hydrophilic material, e.g., one or more of hydroxypropylmethyl cellulose, polyethylene glycol and the like.

Release Modifiers

The release modifiers employed in the polymeric coatings of the invention are generally water-insoluble materials of an inorganic character.

Generally, they are FDA-approved inorganic substances having suitable compatibility with the aqueous polymer dispersions being used. Preferred modifiers are kaolin, talc and titanium dioxide. Kaolin is highly preferred. Mixtures are operable.

While the particle size of the filler is not crucial, it is generally preferred, for ease of handling, that it lie between about 20 $\mu$ (microns) and about 0.001 $\mu$. These particle sizes assure efficient suspension of the inorganic additive in water or water-miscible diluent(s) prior to admixture with the polymeric component.

Milling or other treatment of the additive is not usually required. However, when packaging or storage of the additives has caused agglomeration of particles, minimal milling of the particles, in the presence or absence of aqueous or other suitable media, may be beneficial to the ultimate combining of polymer and release modifying components.

Applicants do not intend to be bound to any particular theory as to the action of the inorganic release modifiers. However, the modifiers appear to function as permeability modifiers in the coatings by virtue of their limited water swellability and bulk. After the coatings dry, the inorganic particles, which are dispersed throughout the coating or film aid in the formation of pores or channels at the interface of the particles and the polymer. It is believed that these pores or channels function as openings through which the body fluid(s) can "leach out" small quantities of the coated drug or other physiologically active substance.

The polymeric coatings of the invention contain, on a dry basis, about 5 to about 95 wt % preferably about 15 to about 75 wt % polymer and about 5 to about 80 wt %, preferably about 10 to about 60 wt % filler. When an aqueous diluent is present, it will generally comprise the balance of the coating.

While plasticizers, solvents, colorants, etc. are not necessary ingredients in all dispersions, they may be used when called for. For example, additional quantities of titanium dioxide may be present to improve the color of the final product. plasticizers may be added to dispersions when the polymer needs plasticization. Generally, however, only aqueous diluent, polymer, and inorganic additives need be present in the instant coatings.

Physiologically Active Substance

The physiologically active substrate which serves as the substance for the coatings of the invention may be one or more of a wide variety of materials. While drugs are preferred, they may also be vitamins, placebos, and the like. Mixtures of such substances can be used. When the active component of the final product is a drug, it is generally a solid substance having sufficient affinity for gastrointestinal fluids to be absorbed by the body once it is contacted with those fluids. Suitable drugs include anti-infective agents, phenols and their derivatives, sulfonamides, sulfones, surfactants, chealating agents, antimalarials, antibiotics, central nervous system depressants, stimulants, adrenergic agents, cholinergic agents, autonomic blocking agents, diuretics, cardiovascular agents, local anesthetics, histaminic and antihistaminic agents, analgesic agents, antitussive agents, steroids, carbohydrates, amino acids, proteins, enzymes, hormones, antiemetic agents, cognition activators, and the like. One preferred group of drugs include pseudoephedrine and theophylline. Mixtures of drugs can be used.

The active component of the dosage forms of the invention will generally comprise about 0 to about 95 wt %, preferably about 5 to about 90 wt %, of the total composition on a dry weight basis, depending upon the dosage of the drug.

Substrates

The coatings of the invention can be used to cover a wide variety of solid substrates. While pellets or cores of active substances are the preferred substrates, other forms can be treated. Tablets, capsules, powders, granules and other forms into which the physiologically active component may be shaped are also operable. The presence of carriers and other conventional ingredients in the active component of the drug can be tolerated. Care should be exercised, however, to exclude degradable, water-soluble, and/or volatile ingredients from both the substrate and the coating. Such exclusion will help assure long shelf life for the final products.

Suitable devices for coating the active substrates include coating pans, fluidized bed devices and the like. In general, those devices suited to the application of water-based coatings to solid substrates can be used.

EXAMPLES

Pellet Preparation: Non-pareil seeds composed of sugar and starch were placed in a prewarmed chamber of a centrifugal granulator. A binder solution of hydroxypropylcellulose was sprayed onto the seeds while simultaneously a meshed powder of each of diphenhydramine hydrochloride, pseudoephedrine HCl and theophylline was fed at an appropriate rate. Once the pellets were made, they were allowed to dry in an oven at 45° for 24 hours. The 12–18 mesh fraction was screened and transferred to plastic bags.

Coating Procedure: Diphenhydramine hydrochloride, pseudoephedrine and theophylline pellets were coated with mixtures of kaolin and Eudragit E 30 D dispersion. The preparation of the coating formulations involved formation of a suspension of untreated kaolin using a magnetic stirrer followed by intimate mixing of the suspension with the desired quantity of the polymeric dispersion. The pellets (300 gm in weight) were initially coated with the coating formulations set out in Table I slowly in fluidized bed equipment, i.e., a device, at about 1.0 ml per minute until their weight was increased by approximately 3%. They were then dried for 30 minutes using the fluidizing air while still in the chamber. Coating was then resumed at a faster rate. The formulation was stirred throughout the coating process. The coated pellets were transferred to a paper-lined tray and dried under air. Kaolin was used as received but can also be ball-milled if necessary. Eudragit E 30 D was filtered through a fine sieve (120 mesh) before use in order to remove solid or film particles.

Dissolution: In vitro dissolution studies were carried out using the USP dissolution apparatus II at 37° and 75 rpm. The dissolution media were water, simulated (without enzymes) gastric fluid and/or intestinal fluid. Samples were withdrawn and dissolution medium replaced automatically at preselected time intervals. Assay of the released drug was conducted spectrophotometrically at 258 nm.

TABLE I

| Drug | Coating Formulations | | |
|---|---|---|---|
| | E 30 D (gm) | Kaolin (gm) | Water (gm) |
| Diphenhydramine hydrochloride | 200 | 20 | 180 |
| Pseudoephedrine hydrochloride | 200 | 40 | 427 |
| Theophylline | 200 | 60 | 540 |

EXAMPLE 1

Diphenhydramine hydrochloride pellets produced as described above and having a final coating weight of 20 wt % were compared to overcoated diphenhydramine hydrochloride pellets for release rates.

The overcoated pellets were prepared by subjecting the singly coated pellets to an additional coating with an overcoat formulation. That overcoat contained hydroxypropylmethylcellulose and was applied to give a final coating weight of 2 wt %.

The results of the release studies, which were conducted in accordance with the dissolution procedure described above, are given in Table II.

TABLE II

| Release Data of Diphenhydramine Hydrochloride Pellets With and Without an Overcoat | | |
|---|---|---|
| Time (hrs.) | Percent Release | |
| | With Overcoat | Without Overcoat |
| 0.5 | 4 | 3 |
| 1 | 9 | 8 |
| 2 | 33 | 33 |
| 4 | 56 | 56 |
| 6 | 69 | 69 |
| 8 | 77 | 77 |
| 10 | 82 | 82 |
| 12 | 85 | 85 |

DRAWINGS

FIG. I represents a release curve (derived by plotting cumulative percent released versus time) for pseudoephedrine, i.e., hydrochloride in each of the fluids indicated. The pellets were prepared and the dissolution studies were carried out as described above.

FIGS. II through VI were derived using the respective coatings, coating levels and dissolution media indicated thereon.

As these examples and the drawings indicate, the rate of drug release from the dosage form is directly proportional to the ratio of kaolin to polymer in the final film or coating. FIG. II shows changes in kaolin/resin ratio vs. release rate.

Optimally, a second coating or overcoat can be applied in order to minimize handling problems. For example, the soft lumps that are often observed when coated pellets were stored at room temperature were eliminated by applying a water-soluble overcoat. The overcoat, which was composed of less than 2% by weight of hydroxypropylmethylcellulose, did not in any way affect the rate or extent of drug release.

The release rate for dosage forms made using the instant coatings can be adjusted by varying such parameters as release modifier concentration (see FIG. IV) and coating level or thickness (see FIG. III). For example, the amount of kaclin or other modifier in the coating formulation can be increased to the point that film integrity is lost and immediate drug release occurs.

Likewise, a coating layer of insignificant thickness would be an inefficient barrier to release. Generally coating thicknesses corresponding to an overall coating/active component (e.g., coating/drug) ratio of about 2 to about 98% are desirable. Preferably, a coating/drug ratio on the order of 10 to 90% is used depending on dose and physical chemical characteristics of the drug.

Reasonable variations, such as those which would occur to a skilled artisan, can be made herein without departing from the scope of the invention.

We claim:

1. A coating composition for sustained release dosage forms which consists of a suspension of kaolin in water combined with an aqueous dispersion of a copolymer of poly(meth)acrylic esters.

* * * * *